United States Patent [19]
Williams et al.

[11] Patent Number: 4,679,075
[45] Date of Patent: Jul. 7, 1987

[54] GLASSWARE INSPECTION USING OPTICAL STREAK DETECTION

[75] Inventors: Reade Williams, South Hamilton; Kenneth P. Westlund, Danvers, both of Mass.

[73] Assignee: Emhart Industries, Inc., Farmington, Conn.

[21] Appl. No.: 728,054

[22] Filed: Apr. 29, 1985

[51] Int. Cl.$^4$ .............................................. H04N 7/18
[52] U.S. Cl. .................................... 358/106; 358/101; 358/107; 250/223 B; 356/237; 356/239; 209/939; 209/526
[58] Field of Search ........................ 358/106, 107, 101; 250/223 B, 223 R; 356/237, 239, 240; 209/524, 526, 939

[56] References Cited
U.S. PATENT DOCUMENTS

| | | | |
|---|---|---|---|
| 4,256,957 | 3/1981 | Ford | 250/223 B |
| 4,280,624 | 7/1981 | Ford | 209/524 |
| 4,414,566 | 11/1983 | Peyton et al. | 358/101 |
| 4,488,648 | 12/1984 | Claypool | 209/526 |
| 4,492,476 | 1/1985 | Miyazawa | 250/223 B |

Primary Examiner—Howard W. Britton
Assistant Examiner—John K. Peng
Attorney, Agent, or Firm—Arthur B. Moore; Arthur J. Samodovitz

[57] ABSTRACT

Method and apparatus for inspecting transparent articles such as glassware for various types of defects, while conveying the articles past an optical inspection assembly. An article to be inspected is transported through an inspection station where it may undergo rotational and translational motion while being illuminated during an inspection interval. The inspection apparatus includes a video camera which provides output signals representative of the luminance of image elements, and video processing circuitry to derive line sum signals representative of the aggregate luminance of preselected scan lines. The line sum signals are further processed to discriminate streaks of brighter-than-normal or darker-than-normal pixels in a series of image frames. The user may establish window parameters to define an area of the article to be scanned for defects.

24 Claims, 17 Drawing Figures

GLASSWARE INSPECTION USING OPTICAL STREAK DETECTION

BACKGROUND OF THE INVENTION

The present invention relates to the optical inspection of glassware and like transparent articles, and more particularly to inspection of transparent articles for defects during translation or rotation past an optical inspection station.

It is well known to provide automated inspection of glassware and like transparent articles by illuminating the article and optically monitoring light transmitted, refracted, or reflected by the article. Various such techniques rely upon a total or partial occlusion of light rays due to a defect in the article, which is detected as a darker-than-normal spot in the image. Alternatively, light may be reflected by a defect toward the photosensor, resulting in a brighter-than-normal image area. Signal processing circuitry is typically employed to amplify and shape the photosensor output, for comparison to preselected threshold values indicative of faults. These techniques have typically suffered "false positives" and "false negatives" due to random light patterns, container surface characteristics, artifacts, crosstalk in the inspection electronics, and other illusory effects.

One factor of critical significance in the operation of such inspection systems is the motion, if any, which the article may undergo during the inspection period. The usual approach has been to control article motion during inspection to provide an angular displacement over time between the article and the photosensor. Specialized conveyor apparatus may be required for this purpose.

U.S. Pat. No. 4,256,957 to Ford et al. discloses bottle inspection apparatus wherein an image of a bottle area is projected onto an array of photodiodes to derive a video signal based upon a sequence of light energy readings from individual pixels. This signal is differentiated to provide a "differentiated frame video signal" representative of the outputs of successive whole row of photodiodes. The Ford et al. device permits the inspection of bottles travelling on high speed conveyors by limiting the inspection interval to around 1 millisecond. As such, their system is unsuitable for "real time" inspection of glassware containers, for example while rotating the container to scan the entire circumference. This system will therefore be vulnerable to illusions which might lead to invalid data at a given scanning configuration.

U.S. Pat. No. 4,280,624 to Ford teaches apparatus for inspecting the sidewalls of bottles in which a plurality of sidewall images are projected from two or more different directions onto one or more photodiode arrays, thereby to scan the entire bottle circumference. This approach suffers the shortcoming mentioned above of vulnerability to illusory readings which may occur in a given bottle position or orientation.

Commonly assigned U.S. Pat. No. 4,488,648 to M. Claypool relies upon an optically generated signal which is processed in real time by repetitively calculating the time rate of change and comparing these calculations to preselected values as a basis for fault rejection. This technique represents a useful advance over the prior art, but requires relatively complicated preliminary analysis as a prerequisite to inspection.

U.S. Pat. No. 4,492,476 to Miyazawa discloses a defect inspection technique for bottles wherein the bottle is conveyed while being spun, and video images thereof are acquired sequentially and repeatedly in the form of a plurality of picture elements. Picture element signals on an imaginary line perpendicular to the central axis of the image are compared, and the results of this comparison are processed to discriminate defects. This technique does not achieve a principal advantage of applicants' technique of effectively reducing the likelihood of falsely identifying spurious signals, random light patterns, etc. as defects.

Accordingly, it is a principal objective of the invention to provide improved method and apparatus for automated optical inspection of glassware articles and the like. A related object is to provide a reliable technique for identifying features of an article which is moving relative to a photoinspection device.

A further object is to effectively discriminate between features of interest in such articles and illusory phenomena, such as random light patterns, artifacts, and camera electronics crosstalk.

A still further object is to adapt this technique to the detection of brighter-than-ambient image features, as well as darker-than-ambient features.

SUMMARY OF THE INVENTION

The above and additional objects are successfully realized in the optical inspection method and apparatus of the invention, which utilizes a "streak detection" technique to identify defects in glassware articles and the like. This technique relies upon the scanning by a photosensor of an article undergoing relative motion along a motion axis, to acquire video data along a plurality of scan lines. Advantageously, the scan lines are oriented essentially parallel to the motion axis. This scan line information is processed by a Video Processor assembly, along with timing and control signals, to derive output signals representative of optical row sums, i.e. integrals of the video signals along individual scan lines or rows of the video data. Video data acquisition and processing occurs for a plurality of video frames in real time, so that successive optical signal frames represent successive positions of the article relative to the photosensor. In the preferred embodiment, the photosensor comprises a solid state CCD camera, which acquires analog video data in the form of rows and columns of VIDEO pixel signals.

The streak detection technique of the invention takes advantage of the relative motion between article and photosensor, parallel to the scan lines. The presence of a brighter-than-ambient (or, in the alternative embodiment, darker-than-ambient) image feature along a given scan line or row generates a streak in that row of video data. Optical row sum signals derived from such video data will contain a large numerical contribution from the streak, effectively de-emphasizing random light patterns, camera crosstalk effects, and other spurious sources (which will not generate large contributions to the optical row sums).

The resulting line sum arrays for the plurality of optical signal frames are further processed to discriminate optically significant features. Preferably, this processing identifies maxima among the optical line sums to discriminate the presense and possibly placement of defects. Such processing may involve the comparison of a plurality of row sum arrays for multiple image frames.

In the preferred embodiment, the optical row sums are compared to provide a set of absolute difference arrays. Where one or more rows of successive line sum arrays contain a large numerical contribution from a bright (or dark) streak, this will appear as a local maximum or peak in the processed video signals. A Streak Detection technique interprets the aggregate differentiated line sum arrays to discriminate significant optical streaks and recognize the presence of a defect. The user may select a threshold signal-to-noise ratio below which processed video peaks will not be recognized as optically significant.

A principal aspect of the invention relates to the relative motion between the article and a photosensor device, which motion generates the video streaks characteristic of the invention. In the preferred embodiment, the article is rotated to provide a circumferential optical scanning of the outer sidewall, desirably while also translating the article. The alignment of the photodetector, axis of rotation, and translation axis are chosen so that the article moves along a given, illustratively horizontal axis (the "motion axis") during the acquisition of frames of video data. The apparatus acquires a plurality of video image frames in real time to ensure complete circumferential inspection of the article. A Video Processor circuit integrates gray scale pixel values along parallels to the axis of article motion, providing a line sum for each scanning line. The line sum of a horizontal scan line which coincides with a horizontal bright (or in the alternative-embodiment, dark) streak will contain a large numerical contribution from the streak.

A further aspect of the invention is the profile of an area of the article to be scanned within a composite image frame, effected by a Window Definition subcircuit. This assembly receives data which may be user-prescribed or automatically defined, indicating for each horizontal scan line the start and stop pixels in the scan. This data also includes the uppermost and lowermost scan lines to be included in the window. Optionally, a gain register may include an array of values, one for each horizontal scan line, allowing the user to determine the relative weights given the various optical line sums.

An advantageous application of this optical inspection apparatus is in the bright streak detection of inner-wall defects in cylinderical glassware articles. Commonly assigned U.S. patent application Ser. No. 707,267 in the names of P. F. Scott and D. J. Brady, "Birdswing Defect Detection for Glass Containers", filed on Mar. 1, 1985, discloses a bottom illumination technique which results in bright spots in a video image taken on a normal to the outer sidewall of a glass container. Where such an article is rotating relative to a video camera or like device, birdswings are observable in chronologically sequential image frames as horizontal bright streaks. The method and apparatus of the invention is also advantageously applied, however, to dark streaks resulting from locally occluded light.

BRIEF DESCRIPTION OF THE DRAWINGS

The above and additional aspects of the invention are illustrated in the detailed description of the preferred embodiment which follows, which is to be taken in conjunction with the drawings in which:

FIGS. 6B–6E plot video potentials over a given horizontal line scan at various stages of the video processing technique of the preferred embodiment, for the bottle shown in section in FIG. 6A:

DETAILED DESCRIPTION

Figure 1:
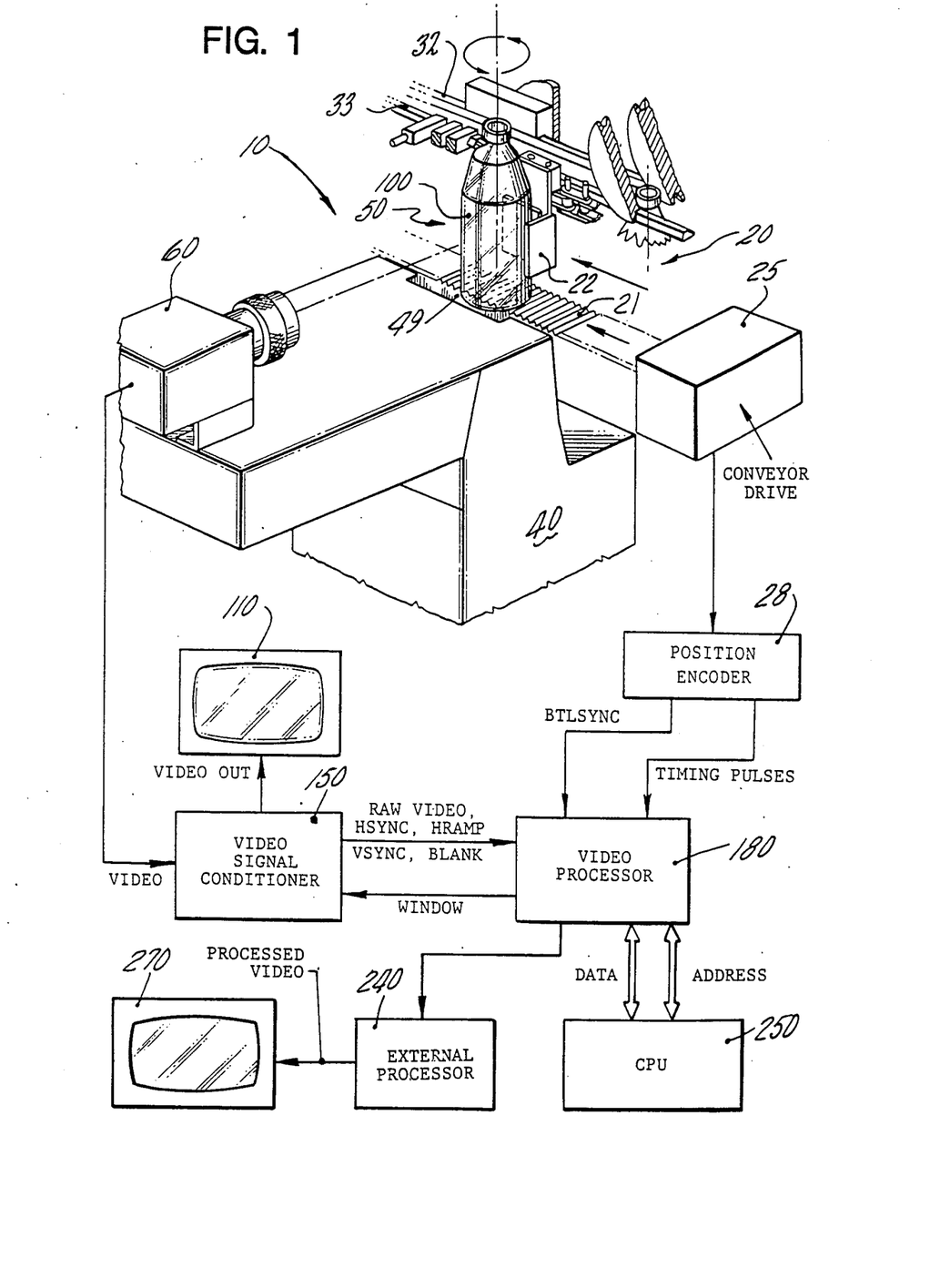
FIG. 1 is a somewhat schematic view of optical inspection apparatus according to the preferred embodiment.

Reference should now be had to FIG. 1, which illustrates a preferred form of optical inspection apparatus utilizing the streak detection technique of the present invention. Inspection apparatus 10 has particular utility in detecting flaws in glassware containers and like transparent or translucent articles. Inspection apparatus 10 includes ware transport 20, having an underlying conveyor 21 and wareholding flanges 22 for linearly transporting article 100 through the inspection site 50, and overhead belts 32 and 33 which nip the finish of the container 100 and rotate it during inspection. Belts 32 and 33 are driven to rotate bottle 100 several times during the inspection interval. The conveyor drive assembly 25 for transport 20 interacts with a position encoder 28, which provides a BTLSYNC index signal once per transport cycle, as well as timing pulses which are correlated with the translational velocity of article 100. As explained below, these signals are received by Video Processor 180 to control the operation of this circuit in real time.

The illustrated apparatus 10 incorporates an illumination assembly 40 in accordance with commonly assigned co-pending application entitled "Birdswing Defect Detection for Glass Containers", of P. F. Scott and D. J. Brady, U.S. Ser. No. 707,267, filed Mar. 1, 1985. Assembly 40 projects a band of light through slot 49, which light is selectively reflected by inner-wall defects in bottle 100 so as to emerge along a normal to the outer sidewall. The video camera 60 scans a predetermined region of the article 100, as disclosed in detail herein, and detects the reflected light rays as bright streaks in the scanned image. The video processing apparatus of the present invention is well suited to discriminating such bright streaks and thereby recognizing birdswings and like defects. It should be understood, however, that the optical inspection technique and apparatus of the present invention is not restricted to a given illumination scheme or bottle-handling arrangement, and has applicability to a variety of inspection set-ups, and to the detection of light which is reflected or transmitted by flaws. In fact, the present technique is equally well suited to the discrimination of darker-than-normal image features such as those characteristic of back-lighting schemes. This apparatus enjoys particular utility in the scanning of a sidewall of a circumferentially rotated article, as shown in FIG. 1.

The preferred, illustrated inspection appartus incorporates a solid state CCD camera to monitor light from container 100 and form frames of gray scale VIDEO signals, in which the voltage of given frame elements is representative of the luminance of a corresponding area of the scanned image. Illustratively, each video frame from CCD camera 60 comprises a rectangular matrix of X (horizontal) by Y (vertical) pixels. It is important to properly orient camera 60 relative to bottle 100 so that the horizontally scanned rows of pixels are aligned essentially perpendicularly to the axis of rotation of bottle 100 and parallel to the bottle's axis of translation. In this way the pixel rows will be parallel to the axis of relative motion of article 100. Filtering, spectral sensitivity characteristics of camera 60, integration time, pixel size, and other parameters are tailored to the requirements of a given inspection scheme. Camera 60 constitutes its image frames by transferring the X by Y matrix of photovoltaic pixel charges into an analog shift register, from which they are read serially as VIDEO signals in response to a clock signal from Video Signal Conditioner 150.

The analog VIDEO signals are processed by assemblies 150, 180, and 250. The Video Signal Conditioner assembly 150 accepts composite VIDEO signals from camera 60 (illustratively in the standard RS-170 format), and processes these signals to produce a RAW VIDEO signals, horizontal and vertical sync pulses (HSYNC and VSYNC), horizontal ramp pulses (HRAMP), and blanking pulses (BLANK). These signals are used by Video Processor assembly 180 to generate timing signals and process the RAW VIDEO signals on a line-by-line basis. The Video Processor board generates a WINDOW signal corresponding to a user-selected portion of the video frame from camera 60; the formulation and use of the window signals is explained in detail below. Monitor 110 may be used to display the VIDEO signals, and these may be combined with the WINDOW signals from Video Processor 180 to enable the operator to view the window which is being processed.

Figure 6A:
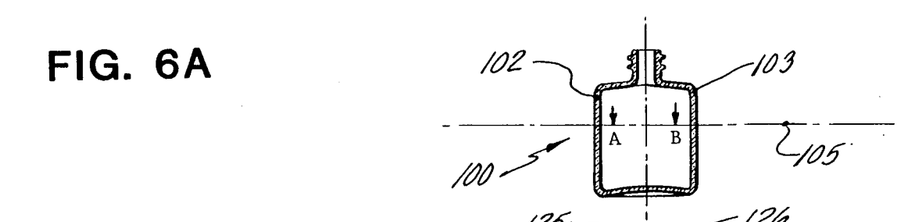
Figure 6B:
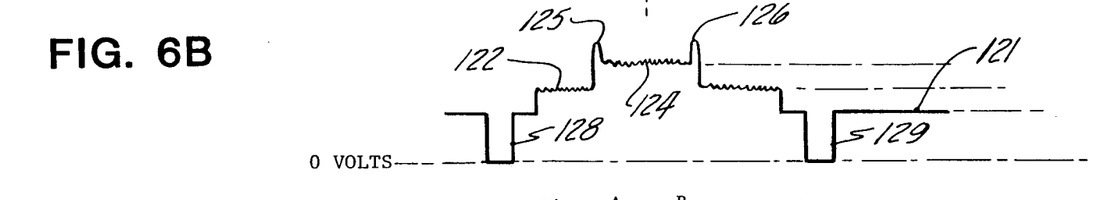
FIG. 6B plots the composite video from the camera.
Figure 6C:
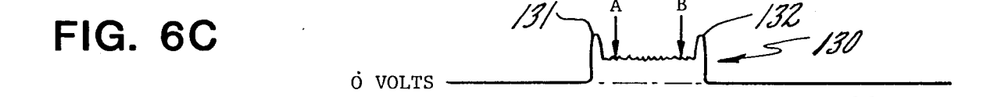
FIG. 6C plots the signal of FIG. 6A after threshold detection.
Figure 6D:
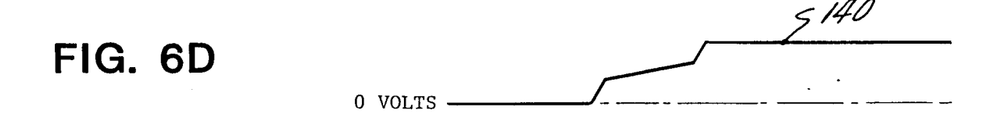
FIG. 6D plots the output of the video line integrator, without window constraints.
Figure 6E:
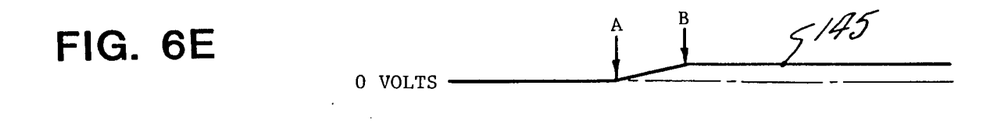
FIG. 6E plots the integrator output with a superimposed window.

In essence, Video Processor 180 integrates the RAW VIDEO signals across each horizontal line subject to the window constraints to provide a vertical array of video line sums. FIGS. 6B-6E give voltage plots of various video signals characteristic of the video processing technique, for a given horizontal scan of the bottle 100 shown in section in FIG. 6A. FIG. 6A shows bottle 100 as viewed by CCD camera 60, indicating a given horizontal scan line 105 which extends through side walls 102 and 103. FIG. 6B plots a composite VIDEO analog signal from CCD camera 60 based upon the scanning of line 105. The characteristic voltage levels include the horizontal "blanking level" 121 (the voltage level of the pedestal signals between horizontal sync pulses 128, 129 in a standard RS-170 television waveform); black background level 122 (voltage signal in the absence of a bottle); the signal 124 during scanning of bottle 100; and the voltage spikes 125 and 126 corresponding to the extreme bottle sidewalls 102 and 103. Video Signal Conditioner 150 strips off the blanking level and black background to produce the RAW VIDEO waveform 130 (FIG. 6C). The line integration circuitry within Video Processor 180 integrates signal 130 as shown in FIG. 6D to achieve a line sum potential 140 for scan line 105. Video Processor 180 enables the user to superimpose window constraints such as left and right limits A and B. By limiting the integration process to this window, the user achieves a more limited line sum (excluding voltage spikes 131 and 132) as indicated at 145 in FIG. 6E.

Figure 2:
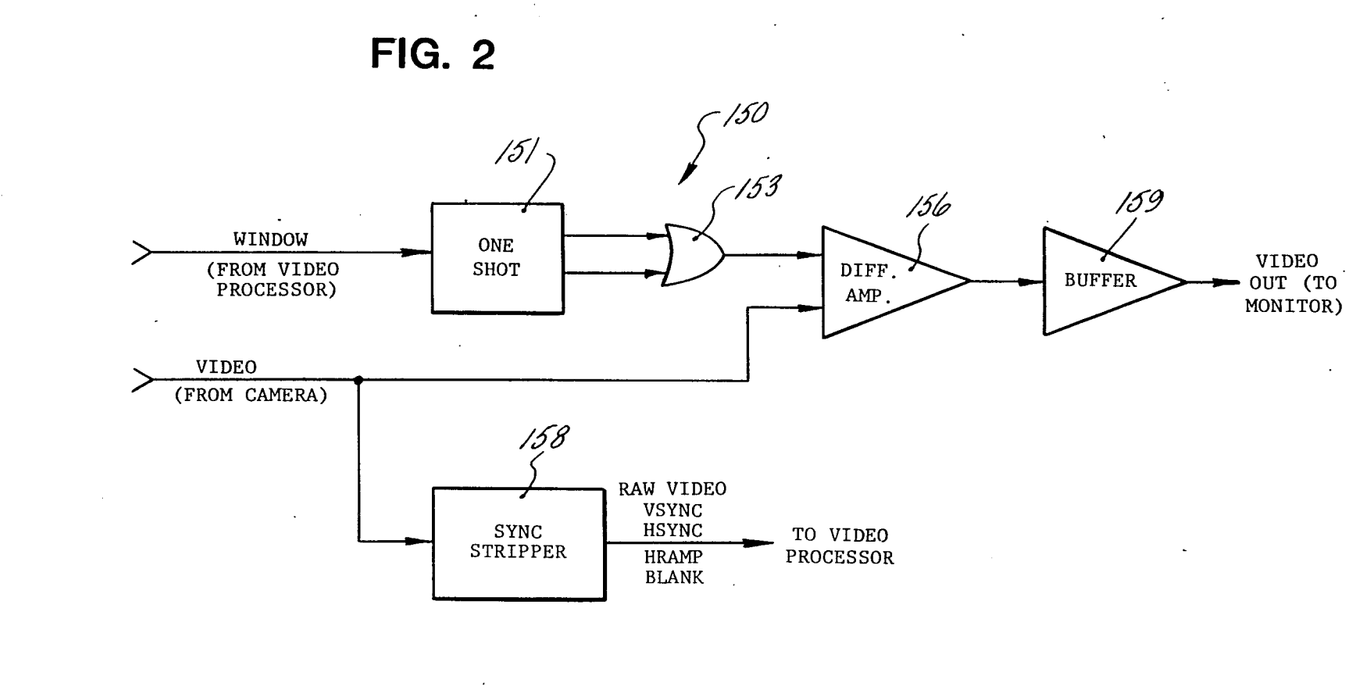
FIG. 2 is a circuit schematic diagram of a basic form of Video Signal Conditioner from the apparatus of FIG. 1.
Figure 3:
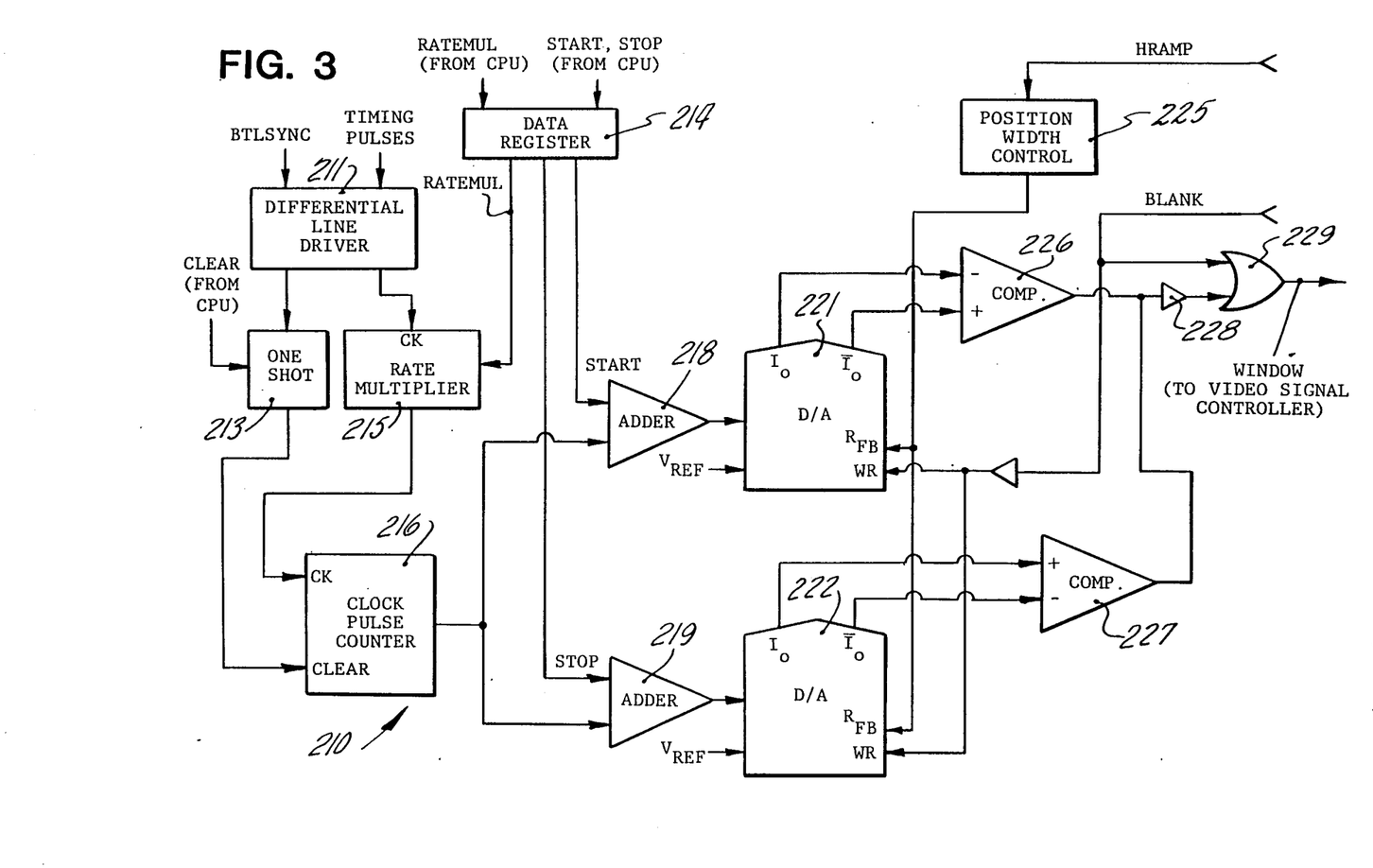
FIG. 3 is a circuit schematic diagram of window definition circuitry within the Video Processor of FIG. 1.
Figures 4, 7:
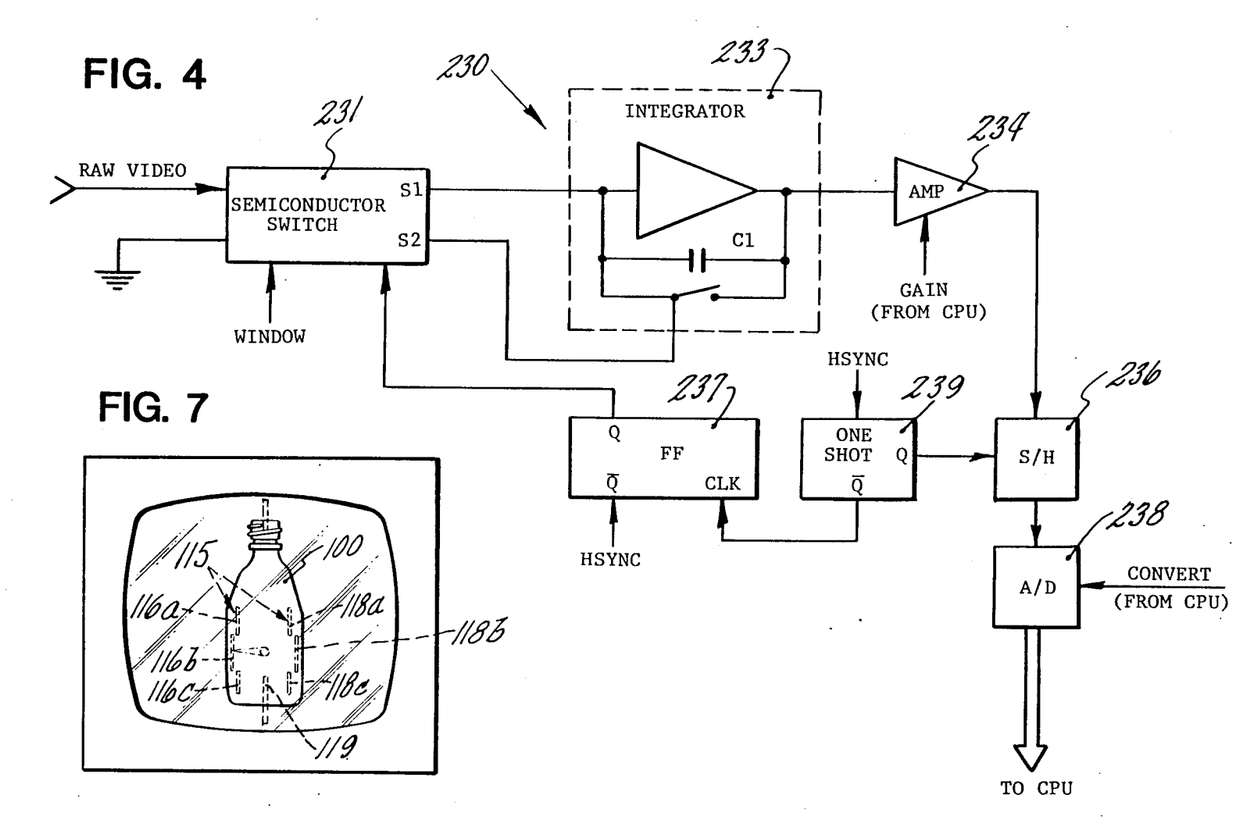
FIG. 4 is a circuit schematic diagram of video integrator circuitry within the Video Processor of FIG. 1.
FIG. 7 is a somewhat schematic view of an illustrative VIDEO OUT display as it would appear in the monitor 110 of FIG. 1.

Reference should now be had to FIGS. 2–4, which show in block diagrammatic form advantageous designs for the Video Signal Conditioner assembly 150 and the Video Processor 180. As seen in FIG. 2 the principal element of the Video Signal Conditioner circuitry 150 is a Sync Stripper 158, which receives the composite VIDEO signals from camera 60 (FIG. 6B). Sync Stripper 158 processes the VIDEO information to output RAW VIDEO signals (FIG. 6C), horizontal sync pulses HSYNC, vertical sync pulses VSYNC, horizontal ramp pulses HRAMP, and blanking pulses BLANK. These signals are used by Video Processor 180 to process the video signal on a line-by-line basis.

The remaining elements of circuit 150 produce a video output signal to permit the operator to observe a window being processed, for user-interactive control. One shot multivibrator 151 receives a WINDOW signal from Video Processor 180, and generates pulses on the leading and trailing edges of this signal. These pulses are OR-gated at 153 and routed to one input of differential amplifier 156, which also receives the composite VIDEO signal. Amplifier 156 sums these signals, and the buffered output 159 VIDEO OUT is sent to monitor 110 (FIG. 1).

FIG. 7 shows an illustrative display on monitor 110 of a window 115 superimposed over the image of a bottle 100 under inspection. When bottle 100 enters the inspection area 50, an INDEX SIGNAL from the position encoder 28, or other signal indicative of the presence of a bottle, initiates video acquisition by camera 60. During set-up of the apparatus 10, the operator directly observes in monitor 110 the image of a bottle 100 placed at the inspection site 50, and can view that portion of the bottle which is being scanned through the display of the window 115. Window 115 is here displayed as left and right boundaries 116 and 118, and window centerline 119. The height of these segments indicates the upper and lower boundaries of window 115. As explained below, the user determines the parameters of window 115 on a line-by-line basis; here left boundary 116 includes segments 116a–116c, with similar segments 118a–118c for right boundary 118, to provide broad and narrow inspection zones.

FIG. 3 illustrates suitable Window Definition circuitry 210 within the Video Processor 180. This assembly generates WINDOW signals using the HRAMP signal from the Video Signal Conditioner circuit 150, the timing pulses from Position Encoder 28, and START and STOP data from CPU 250 (FIG. 1). START and STOP are received through the DATA buss along with data for scaling the external clock signals (time pulses), and stored in data register 214.

Clock Pulse Counter 216 receives the external clock data via differential line driver 211, scaled by Rate Multiplier 215. Rate Multiplier 215 receives RATEMUL at its scale factor input and the timing pulses at its clock input. CPC 216 counts the number of scaled timing pulses since the last BTLSYNC index signal, and is cleared by a pulse from One Shot 213. One Shot 213 may be fired by a signal from DLD 211 in response to a BTLSYNC pulse, or alternatively by a CLEAR signal from CPU 250.

Adders 218 and 219 add the clock pulse counter output to the START and STOP window data from CPU 250, whereby the latter signals are shifted by the clock pulse count. These modified values are applied to the digital inputs of digital-to-analog converters 221 and 222. The internal feedback resistors of D/A's 221 and 222 receive the HRAMP signals from Video Signal Conditioner 150, shifted by precalibrated Position, Width Control 225 which adjusts the horizontal position and width of the window.

Comparator 226, which receives the outputs of D/A 221, goes high when the ramp voltage exceeds the reference voltage $V_{Ref}$ scaled by the digital start data. D/A 220 is connected to comparator 227 to operate in reverse polarity, so that Comparator 227 is high until the ramp voltage reaches the STOP threshold level. The comparator output signals are merged to produce a raw window signal. Gate 229 inhibits the WINDOW function during the retrace or blanking interval. The resulting WINDOW signal is sent to Video Signal Conditioner 150 to permit visual display as discussed above, and to the Video Line Integrator circuit 230 (FIG. 4) to control integration time.

Turning to FIG. 4, element 233 is an analog integrator which integrates the RAW VIDEO data from semiconductor switch 231. Switch 231 control the integration time and integrator discharge time of integrator 233, and illustratively comprises a dual single pole semiconductor switch. One pole S1 of Switch 231 switches between ground and the RAW VIDEO signal under the control of the WINDOW function, and is connected to the integrator input. The other pole S2 is connected to an integrator capacitor C1 and either connects to the other end of the capacitor (during discharge) or is open. When a HSYNC pulse goes low, one shot 235 fires causing sample and hold circuit 236 to sample the input of integrator 233 via amplifier 234, which amplifies the integrator output by the factor GAIN from CPU 250. Advantageously, GAIN values are separately specified for each horizontal line of the image frame, and are reprogrammable by the operator. This allows the user to emphasize or deemphasize selected portions of the video frame in appropriate cases. At the end of this pulse, flip flop 237 is set causing the switch to connect across the capacitor C1. The end of the HSYNC pulse resets FF237 and prepares integrator 233 for the next integration.

The output of S/H 236 is connected to analog-to-digital converter 238, which in turn is linked to memory registers within CPU 250. CPU 250 initiates conversion by A/D 238 through the CONVERT signal, and shortly thereafter acquires the digitalized line sum data via the DATA buss using an interfacing protocol further described below.

Figure 5:
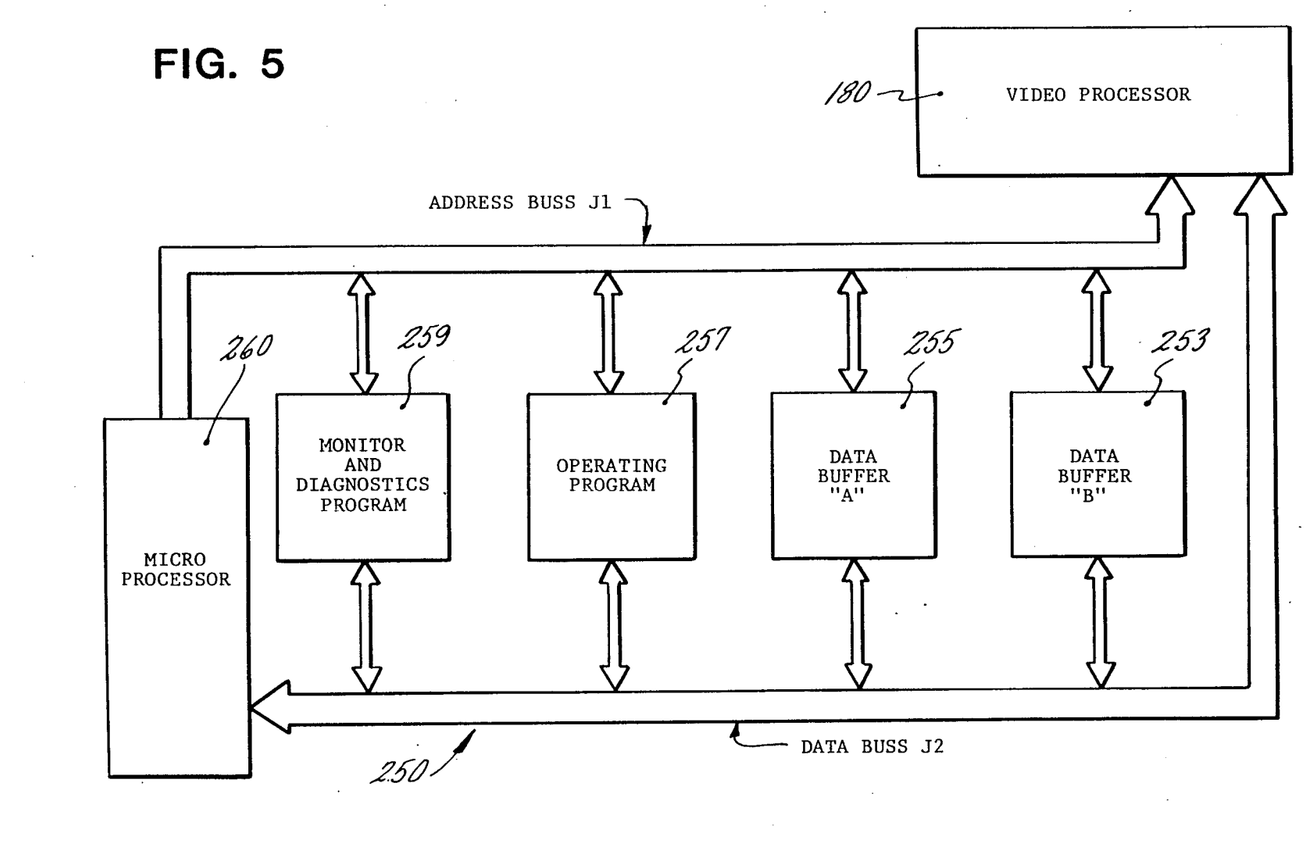
FIG. 5 is a block diagrammatic view of principal elements of the CPU of FIG. 1.

FIG. 5 gives a simplified block diagram of illustrative components of CPU 250. The central element of this assembly is microprocessor 260, which controls the functioning of VSC 150 and Video Processor 180 (FIG. 1) by means of control programs stored in read-only memories 257, 259, and supervises video data acquisition by data buffers 253, 255. Memories 257 and 259, which illustratively are EPROMs, respectively store a monitor and diagnostics program (to inspect memory, load diagnostics, etc.) and the standard operating program of the system. The operating program is further explained below with reference to the flow chart diagrams of FIGS. 11–14.

During normal operation the Video "Processor 180" can interface with an external processor, 240 (for control, e.g., of the rejection of bottles 100) via the I/0 port to Video Processor 180 (FIG. 1). This port passes "handshaking" signals that control transmission of data from the data buffers 253 and 255. When one buffer becomes filled, Video Processor 180 sends a flag to the external controller 240 as a signal to transfer the VIDEO data. During an interval in which, e.g., Data Buffer A is filled and available to the external processor, Data Buffer B is loaded from Video Processor 180 with the data for a subsequent frame. The external processor 240 performs further operations on the digitalized line sum array data over a plurality of image frames to provide PROCESSED VIDEO signals, which are used for the defect recognition decision. PROCESSED VIDEO signals may also be displayed on monitor 270.

Figure 8:
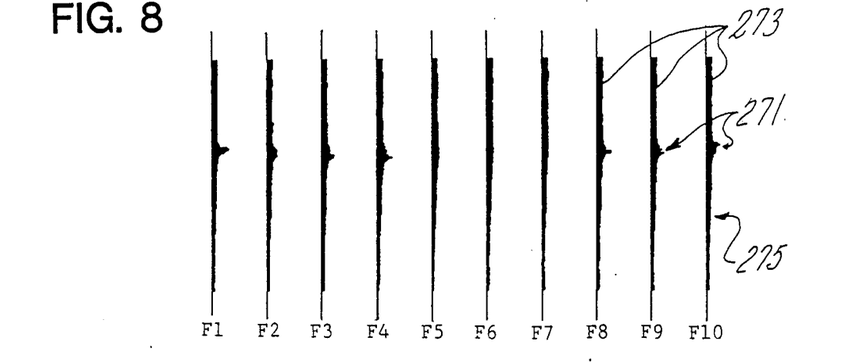
FIG. 8 plots an illustrative set of video line sum displays.
Figure 9:
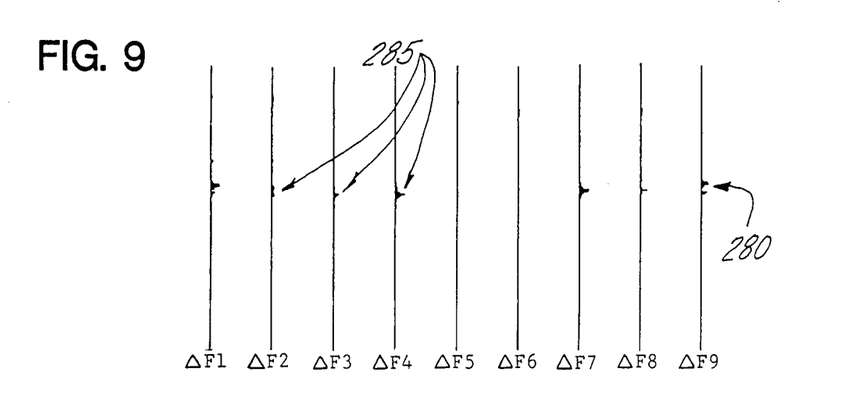
FIG. 9 plots a set of line sum difference displays derived from the line sum displays of FIG. 8.
Figure 10:
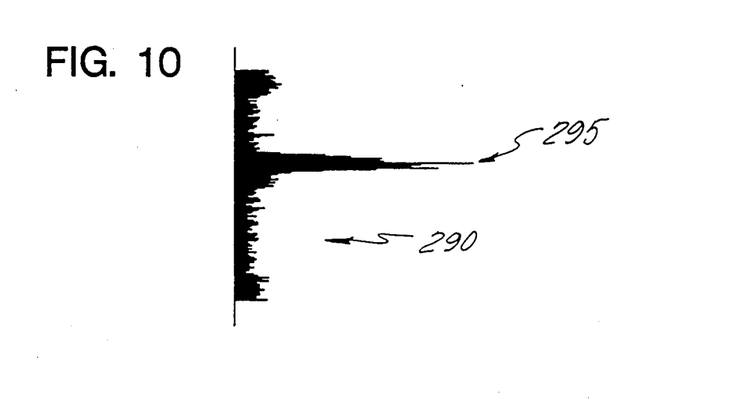
FIG. 10 plans an aggregate video differential display derived from the displays of FIG. 9.

FIGS. 8–10 give various PROCESSED VIDEO signal illustrating the type of video information typically displayed on monitor 270. Video line sum arrays are stored in memory by CPU 250 on a frame-by-frame basis. As video data is acquired in real time, successive displays F1, F2 etc. (FIG. 8) represent line sum arrays (one per video frame) obtained at successive orientations and translational positions of bottle 100 relative to camera 60. Those video row sums which include significantly brighter-than-normal elements (i.e. bright streaks) will appear as peaks 271 within the frame displays. In addition there will be background signal 273 which is relatively constant throughout signals 275. As indicated in FIG. 9, a series of frame difference signals F1=F2-F1, F2=F3-F2, etc. reveal any significant variations between successive line sum arrays. Local "bright streaks" will appear as a peak 271 in only those processed video frames containing the streaks within the predefined window. Thus, signals 280 essentially cancel out the background signal levels representative of ambient luminance, and leave only singularities 285 indicating an increase or decrease between corresponding line sums of adjacent image frames.

At the final stage of the image analysis of the preferred embodiment, the various line sum array difference signals 280 (FIG. 9) are summed to provide an aggregate signal over a preselected number of frames—in this case ten. FIG. 10 shows the aggregate signal 290 derived from the displays of FIGS. 8 and 9, including a prominent peak 295. This aggregate signal will reflect genuine local features of article 100, which will induce horizontal streaks in one or more rows of the PROCESS VIDEO data, while tending to cancel out spurious signals caused by random light patterns, artifacts, camera cross-talk, etc. Applicants have observed in the apparatus of the preferred embodiment that the ratio of the amplitude of signal peak 295 to the average amplitude of signal 290 gives a fairly accurate indication of the presence or absence of a genuine optically-detected flaw in bottle 100. Where employing this algorithm for a ware reject decision the user may empirically determine a cut-off ratio above which bottles 100 will be rejected.

It should be emphasized that the method for processing the line sum arrays which has been illustrated with reference to FIGS. 8–10 is only one of a variety of interpretive techniques which may be employed in implementing the present invention.

Figure 11:
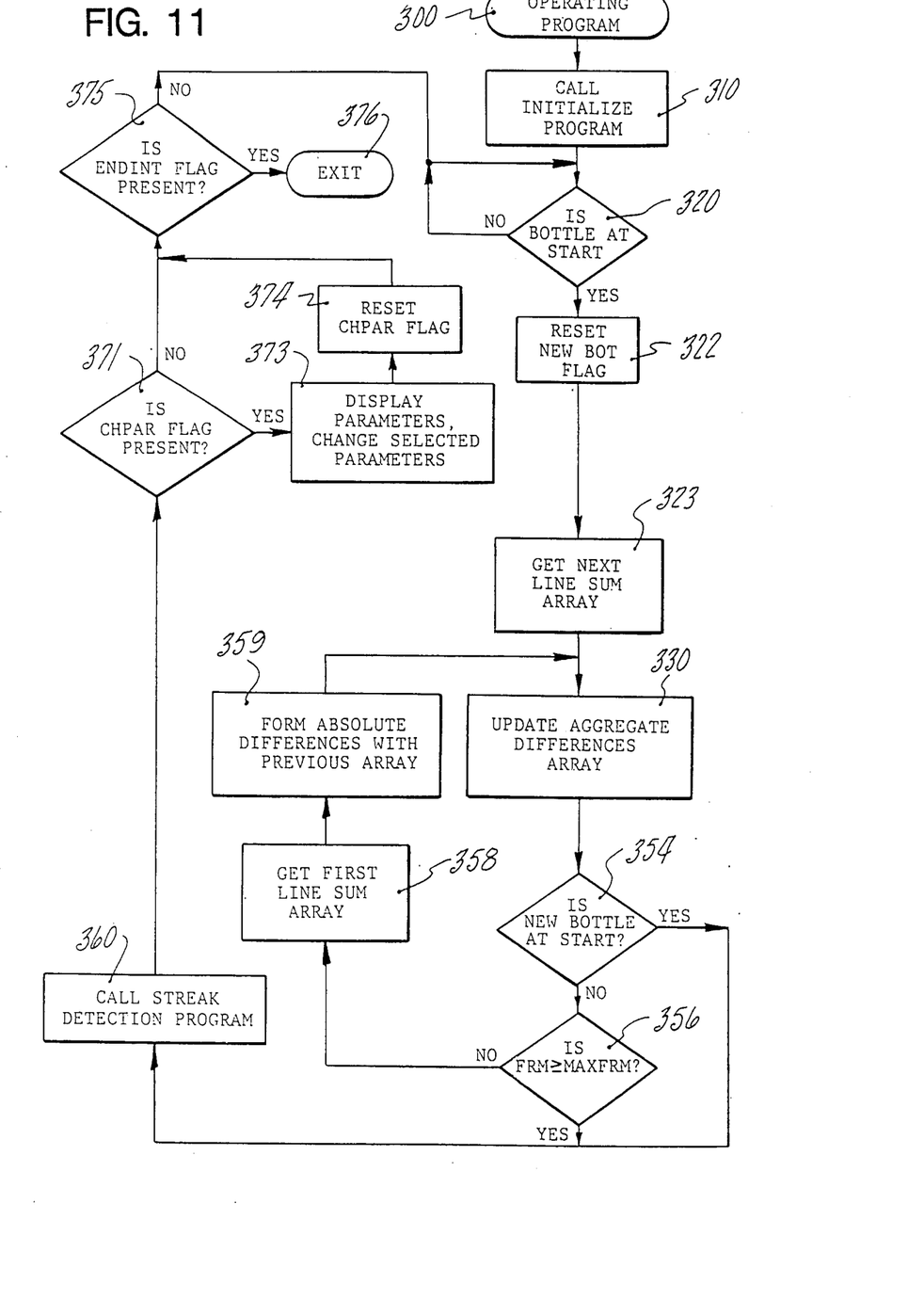
FIG. 11 is a flow chart schematic diagram of an operating program for the apparatus of FIG. 1.
Figure 12:
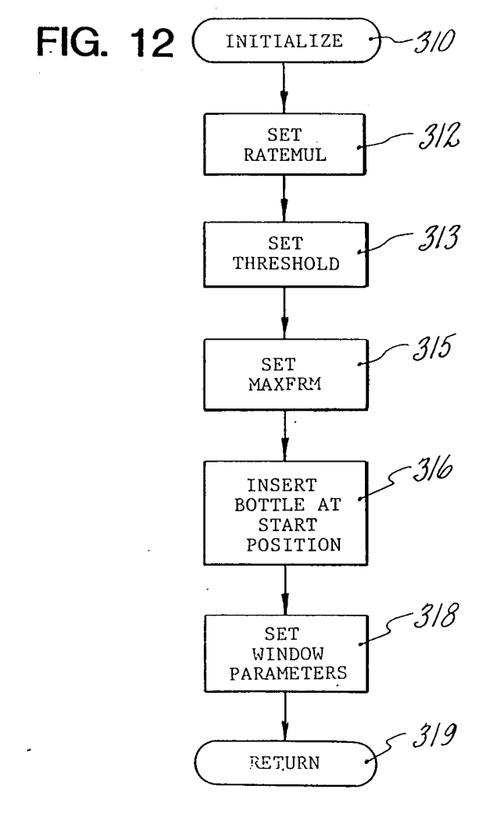
FIG. 12 is a flow chart schematic diagram of an Initialization subprogram for the operating program of FIG. 11.

FIGS. 11–14 illustrate in flow chart block diagrams a suitable operating program for apparatus 10, to be stored in read-only-memory 259 (FIG. 5). The initial stage of Operating Program 300 (FIG. 11) calls an Initialize Subprogram 310, which enables the user to preselect various significant operating parameters. With reference to FIG. 12, at step 312 the user establishes the multiplier RATEMUL which provides the proportionality factor for real time control of Video Processor 180 using the timing pulses from Encoder 28 (FIG. 1). The operator then sets the THRESHOLD value which quantifies the minimum significant level of optical streaks (discussed above with reference to FIG. 10). MAXFRM, set in step 315, is the maximum number of frames to be processed by apparatus 10 in the inspection of a given bottle 100. The user next inserts a sample bottle 100 in the Start position at inspection site 50, i.e. the point at which scanning of a new bottle by CCD 60 begins. Having reference to a video display such as shown in FIG. 7, the operator selects the Window Table values—i.e. the top and bottom row in each frame which is to be processed (TROW and BOTROW), and for each row, the left-most and right-most columns LCOL and RCOL, and the integration factor GAIN. The system then reverts to the principal program.

With further reference to FIG. 11, after initialization the program idles at 320 until a new bottle is detected in the start position, via the INDEX signal from position encoder 28, which sends the NEWBOT flag. This flag is reset in step 322. External processor 240 is then instructed to get the first VIDEO line sum array from CPU 250. The compilation of given line sum arrays is a hardware function, described above.

At 330 the external processor 240 is instructed to update its aggregate array of difference values (cf. FIG. 10). Steps 354 and 356 cause the program to exit from the LINE SUMS loop if a new bottle has been detected at the start position, or if the frame counter FRM has reached the maximum frame value MAXFRM. Failing either of these conditions, the external processor 240 is loaded with the next frame of line sum arrays at 358, and computes the absolute difference value between the line sum values of the last-compiled frame and the previous frame (of FIG. 9).

Figure 13:
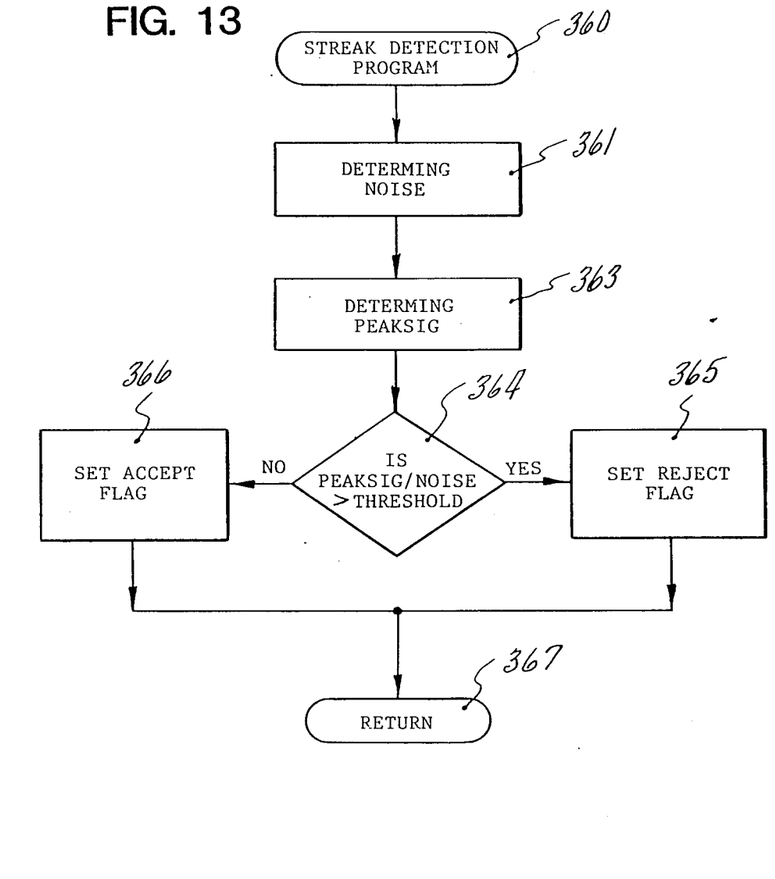
FIG. 13 is a flow chart schematic diagram of a Streak Detection subprogram for the operating program of FIG. 11.

Upon exiting from the LINE SUMS loop, Operating Program 300 calls the Streak Detection Program 360, which provides a decision algorithm for optically significant defects in articles 100. Reference shall now be had to FIG. 13, which illustrates a preferred algorithm for interpreting the line sums data. At 361, CPU 250 computes the NOISE level of the aggregate signal 290 (i.e. the averaged signal value), and the peak signal value 295 (of FIG. 10). The ratio of these values is compared with the user-selected THRESHOLD value at 364, leading either to an ACCEPT decision 366 or REJECT decision 365.

Referring again to FIG. 11, after exiting from the decision program 360, the operating program permits resetting of parameters upon recognition of a CHPAR flag at 371, 373, and 374, and termination of the program at 375, 376. Absent an ENDINT flag, the system returns to its idle state pending the arrival of a new bottle.

While reference has been made above to specific embodiments, it will be apparent to those skilled in the art that various modifications and alterations may be made thereto without departing from the spirit of the present invention. For example, the line sum integration technique may be combined with a modified procedure for processing the line sum data to alter the decision algorithm. Therefore, it is intended that the scope of this invention be ascertained by reference to the following claims.

We claim:

1. A method for inspecting articles for manufacturing defects, said method comprising the steps of:
    illuminating an article to be inspected;
    optically scanning a portion of the article with an optical scanner during an inspection interval while causing relative motion between the article and the optical scanner, said optical scanner comprising a matrix of video elements arranged in rows and columns, and said relative motion being great enough to cause said optical scanner to register a streaked image;
    deriving a series of chronologically sequential frames from said optical scanner corresponding to output signals of the matrix of video elements, and
    for each of a plurality of linear portions of each frame, summing the output signals of the corresponding video elements to identify an image streak registered in at least one of said linear portions representing a defect in the article.
    comparing said line sum signal arrays with a predetermined defect standard to determine any row or rows of the arrays which signifies the presence of a defect in the article.

2. A method as defined in claim 1, wherein the article is illuminated upwardly through its base and a side of the article is optically scanned to sense defects in response to recognition of brighter-than-ambient image streaks.

3. A method as defined in claim 1, for sensing defects in response to the recognition of darker-than-ambient image streaks.

4. A method as defined in claim 1, wherein the relative motion between the article and the optical scanner occurs along a motion axis, and the video elements corresponding to the linear portions are oriented essentially parallel to the motion axis.

5. A method as defined in claim 4 wherein the relative motion is caused at least in part by rotating the article about its central axis.

6. A method as defined in claim 4 wherein said motion axis is parallel to said rows of video elements so that a streak extends longitudinally of at least one of said rows, and further comprising the step of predetermining a portion of the matrix of video elements for which the summing step is effected.

7. A method as defined in claim 6, further comprising the step of assigning a gain factor to each row of the optical signal frames, by which the sum of the output signals for that row is to be multiplied.

8. A method as defined in claim 1, wherein the sums of the output signals for each said linear portion of each frame provide an array of line sum signals and further comprising the step of generating differential signal arrays representing the absolute differences between line sum signal arrays of consecutive frames.

9. A method as defined in claim 8, further comprising the steps of:
   adding together the differential signal arrays representing an article to yield an aggregate signal array; and
   comparing a predetermined characteristic of the aggregate signal array with a defect standard to determine whether a defect is present.

10. A method as defined in claim 9, wherein the predetermined characteristic of the aggregate signal array comprises the ratio of its peak signal value to its average signal value.

11. A method as defined in claim 10 wherein the series of chronologically sequential optical signal frames are based upon at least one complete circumferential scanning of the article.

12. In a system for inspecting translucent articles for manufacturing defects, including movement means for transporting and rotating an article under inspection, the improvement comprising:
   optical scanning means for generating sequential frames of video signals representative of the optical image of at least a portion of the article, said video signal frames comprising rows and columns of video elements, the region of the article scanned by rows of video signal elements being oriented essentially parallel to the direction of the relative motion between the article and the optical scanning means;
   means for summing electrical output signals of a series of said video signal elements in each of a plurality of said rows to generate line sum signals arrays for each video signal frame; and
   electronic processing means responsive to the line sum signal arrays for identifying streaks in rows of video elements.

13. Apparatus as defined in claim 12, wherein the processing means comprises means for producing differential signal arrays representative of absolute differences between line sum signal arrays of consecutive frames.

14. Apparatus as defined in claim 13, further comprising:
   means for deriving an aggregate signal array from a sum of the differential signal arrays; and
   means for comparing a predetermined characteristic of the aggregate signal array with said defect indicators to determine whether a defect is present in said article.

15. Apparatus as defined in claim 14, wherein the predetermined characteristic of the aggregate signal arrays comprises the ratio of its peak signal value to its average signal value.

16. Apparatus as defined in claim 13, further comprises timing signal generating means for coordinating the pace of the summing means with the speed of the transporting means.

17. Apparatus as defined in claim 13, further comprising window definition means for storing user-programmable row and column values specifying given video signal elements to be summing by said processing means.

18. Apparatus as defined in claim 17, wherein the window definition means further comprises means for storing row gain values corresponding to the relative weight to be given to given rows of line sum arrays.

19. Apparatus as defined in claim 13 further comprising means for projecting light upwardly through the base of the article and wherein said optical scanning means is aimed at a side of said article to sense defects in response to the recognition of brighter-than ambient image streaks.

20. Apparatus as defined in claim 13, for sensing defects in response to the recognition of darker-than-ambient image streaks.

21. Apparatus for inspecting translucent articles for manufacturing defects, comprising:
   means for illuminating an article to be inspected;
   an optical scanner for scanning a portion of the article during an inspection interval in which the article and the optical scanner are moved relative to each other, said optical scanner comprising a matrix of video elements arranged in rows and columns, said rows of video elements being oriented essentially parallel to the direction of relative motion;
   means for deriving a series of chronologically sequential frames of optical signals from corresponding output signals of the matrix of video elements;
   means for summing the optical signals corresponding to rows of video elements in order to provide an array of line sum signals for at least a portion of each optical signal frame; and
   video processor means for analyzing the line sum arrays to discriminate maxima, and comparing these maxima with a predetermined defect standard to determine whether a defect is present, the video processor means including means for generating difference signal arrays representative of absolute differences between consecutive line sum signal arrays and producing an aggregate signal array from the sum of difference signal arrays.

22. An apparatus as defined in claim 21, wherein the predetermined defect standard array comprises the ratio of its peak signal value to its average signal value of the aggregate signal array.

23. An apparatus as defined in claim 21, further comprising means for rotating the article about a central axis and a means for conveying the article to provide relative motion between the article and the optical scanner.

24. An apparatus as defined in claim 23 wherein the rotating means operates fast enough in relation to the conveying means such that the series of chronologically sequential optical signal frames are based upon at least one complete circumferential scanning of the article.

* * * * *